United States Patent [19]

Hung et al.

[11] Patent Number: 5,047,241

[45] Date of Patent: Sep. 10, 1991

[54] TRIS-KRINGLE PLASMINOGEN ACTIVATOR WITH NOVEL K2 INSERT

[75] Inventors: Paul P. Hung, Bryn Mawr; Narender K. Kalyan, Phoenixville; Shawguang L. Lee, Villanova, all of Pa.

[73] Assignee: American Home Products Corporation, New York, N.Y.

[21] Appl. No.: 140,068

[22] Filed: Dec. 31, 1987

Related U.S. Application Data

[63] Continuation-in-part of Ser. No. 884,835, Jul. 11, 1986, Pat. No. 4,916,071.

[51] Int. Cl.[5] ..................... A61K 37/547; C12N 9/64
[52] U.S. Cl. ................................ 424/94.64; 435/226; 435/320.1; 536/27
[58] Field of Search ...................... 435/212, 226, 320; 935/14; 536/27; 424/94.64

[56] References Cited

FOREIGN PATENT DOCUMENTS 0178105 4/1986 European Pat. Off. ......... 435/172.3
0213794 3/1987 European Pat. Off. ......... 435/172.3
0225286 6/1987 European Pat. Off. ......... 435/172.3
8703906 7/1986 World Int. Prop. O. ....... 435/172.3

OTHER PUBLICATIONS

Harris, T. J. R., *Protein Engineering*, 1(6): 449–458, 1987.
Van Zonneveld et al, Proc. Natl. Acad. Sci, vol. 83, pp. 4670–4674, Autonomous Functions of Structural Domains on Human Tissue-Type Plasminogen Activator; Jul. 1986.
Vehar, G. et al, Biotechnology, pp. 1051–1057, Characterization Studies on Human Melanoma Cell Tissue Plasminogen Activator; Dec. 1984.
Patthy, Cell vol. 41, pp. 657–663, Evolution of the Proteases of Blood Coagulation and Fibrinolysis by Assembly from Modules; Jul. 1985.

*Primary Examiner*—Richard A. Schwartz
*Assistant Examiner*—Marianne Porta
*Attorney, Agent, or Firm*—Richard K. Jackson

[57] ABSTRACT

Tris-Kringle plasminogen activators containing an additional second kringle domain or an additional modified second kringle domain are useful in disrupting blood clots.

6 Claims, 16 Drawing Sheets

STEP IV

- Subclone in EcoRI cut pUC13
- Screen by
  (a) In situ hybridization with 18 mer probe:

(b) Digestion of plasmid DNA with FspI

```
            10         20          30
     GGGAATTCCG GTACCCATTC CCTGACTGAA
       EcoRl    Kpnl 40         50          60
     AGCGGCGCTA GCTGTCTGCC CTGGAACAGC 70         80          90
     ATGATTCTCA TCGGTAAAGT CTATACCGCT 100        110         120
     CAAAACCCAT CCGCTCAAGC TCTCGGTCTC 130        140         150
     GGTAAGCACA ACTATTGAAG AAACCCCGAC 160        170         180
     GGCGACGCTA AACCATGGTG TCATGTCCTC 190        200         210
     AAAAACAGAC GCCTCACCTG GGAATATTGC 220        228
     GACGTCCCAG AATTCCCG
      Aatll     EcoRl
```

FIG. 3

```
                78                                                    102
        GGATCCCCAG CAATC ATG GAT GCA ATG AAG AGA
                         MET Asp Ala MET Lys Arg

132
        GGG CTC TGC TGT GTG CTG CTG CTG TGT GGA
        Gly Leu Cys Cys Val Leu Leu Leu Cys Gly

162
        GCA GTC TTC GTT TCG CCC AGC CAG GAA ATC
        Ala Val Phe Val Ser Pro Ser Gln Glu Ile

192
        CAT GCC CGA TTC AGA AGA GGA GCC AGA TCT
        His Ala Arg Phe Arg Arg Gly Ala Arg Ser

222
        TAC CAA GTG ATC TGC AGA GAT GAA AAA ACG
        Tyr Gln Val Ile Cys Arg Asp Glu Lys Thr

252
        CAG ATG ATA TAC CAG CAA CAT CAG TCA TGG
        Gln MET Ile Tyr Gln Gln His Gln Ser Trp

282
        CTG CGC CCT GTG CTC AGA AGC AAC CGG GTG
        Leu Arg Pro Val Leu Arg Ser Asn Arg Val

312
        GAA TAT TGC TGG TGC AAC AGT GGC AGG GCA
        Glu Tyr Cys Trp Cys Asn Ser Gly Arg Ala
```

Fig. 8

```
                                        342
CAG TGC CAC TCA GTG CCT GTC AAA AGT TGC
Gln Cys His Ser Val Pro Val Lys Ser Cys

372
AGC GAG CCA AGG TGT TTC AAC GGG GGC ACC
Ser Glu Pro Arg Cys Phe Asn Gly Gly Thr

402
TGC CAG CAG GCC CTG TAC TTC TCA GAT TTC
Cys Gln Gln Ala Leu Tyr Phe Ser Asp Phe

432
GTG TGC CAG TGC CCC GAA GGA TTT GCT GGG
Val Cys Gln Cys Pro Glu Gly Phe Ala Gly

462
AAG TGC TGT GAA ATA GAT ACC AGG GCC ACG
Lys Cys Cys Glu Ile Asp Thr Arg Ala Thr

492
TGC TAC GAG GAC CAG GGC ATC AGC TAC AGG
Cys Tyr Glu Asp Gln Gly Ile Ser Tyr Arg

522
GGC ACG TGG AGC ACA GCG GAG AGT GGC GCC
Gly Thr Trp Ser Thr Ala Glu Ser Gly Ala

552
GAG TGC ACC AAC TGG AAC AGC AGC GCG TTG
Glu Cys Thr Asn Trp Asn Ser Ser Ala Leu
```

Fig. 8a

```
                                        582
GCC CAG AAG CCC TAC AGC GGG CGG AGG CCA
Ala Gln Lys Pro Tyr Ser Gly Arg Arg Pro

612
GAC GCC ATC AGG CTG GGC CTG GGG AAC CAC
Asp Ala Ile Arg Leu Gly Leu Gly Asn His

642
AAC TAC TGC AGA AAC CCA GAT CGA GAC TCA
Asn Tyr Cys Arg Asn Pro Asp Arg Asp Ser

672
AAG CCC TGG TGC TAC GTC TTT AAG GCG GGG
Lys Pro Trp Cys Tyr Val Phe Lys Ala Gly

702
AAG TAC AGC TCA GAG TTC TGC AGC ACC CCT
Lys Tyr Ser Ser Glu Phe Cys Ser Thr Pro

732
GCC TGC TCT GAG GGA AAC AGT GAC TGC TAC
Ala Cys Ser Glu Gly Asn Ser Asp Cys Tyr

762
TTT GGG AAT GGG TCA GCC TAC CGT GGC ACG
Phe Gly Asn Gly Ser Ala Tyr Arg Gly Thr

792
CAC AGC CTC ACC GAG TCG GGT GCC TCC TGC
His Ser Leu Thr Glu Ser Gly Ala Ser Cys
```

Fig. 8b

```
                                    822
CTC CCG TGG AAT TCC ATG ATC CTG ATA GGC
Leu Pro Trp Asn Ser MET Ile Leu Ile Gly

852
AAG GTT TAC ACA GCA CAG AAC CCC AGT GCC
Lys Val Tyr Thr Ala Gln Asn Pro Ser Ala

882
CAG GCA CTG GGC CTG GGC AAA CAT AAT TAC
Gln Ala Leu Gly Leu Gly Lys His Asn Tyr

912
TGC CGG AAT CCT GAT GGG GAT GCC AAG CCC
Cys Arg Asn Pro Asp Gly Asp Ala Lys Pro

942
TGG TGC CAC GTG CTG AAG AAC CGC AGG CTG
Trp Cys His Val Leu Lys Asn Arg Arg Leu

972
ACG TGG GAG TAC TGT GAT GTG CCC TCC TGC
Thr Trp Glu Tyr Cys Asp Val Pro Ser Cys

1002
TCC ACC TGC GGC CTG AGA CAG TAC AGC CAG
Ser Thr Cys Gly Leu Arg Gln Tyr Ser Gln

1032
CCT CAG TTT CGC ATC AAA GGA GGG CTC TTC
Pro Gln Phe Arg Ile Lys Gly Gly Leu Phe
```

Fig. 8c

```
                                              1062
GCC GAC ATC GCC TCC CAC CCC TGG CAG GCT
Ala Asp Ile Ala Ser His Pro Trp Gln Ala

1092
GCC ATC TTT GCC AAG CAC AGG AGG TCG CCC
Ala Ile Phe Ala Lys His Arg Arg Ser Pro

1122
GGA GAG CGG TTC CTG TGC GGG GGC ATA CTC
Gly Glu Arg Phe Leu Cys Gly Gly Ile Leu

1152
ATC AGC TCC TGC TGG ATT CTC TCT GCC GCC
Ile Ser Ser Cys Trp Ile Leu Ser Ala Ala

1182
CAC TGC TTC CAG GAG AGG TTT CCG CCC CAC
His Cys Phe Gln Glu Arg Phe Pro Pro His

1212
CAC CTG ACG GTG ATC TTG GGC AGA ACA TAC
His Leu Thr Val Ile Leu Gly Arg Thr Tyr

1242
CGG GTG GTC CCT GGC GAG GAG GAG CAG AAA
Arg Val Val Pro Gly Glu Glu Glu Gln Lys

1272
TTT GAA GTC GAA AAA TAC ATT GTC CAT AAG
Phe Glu Val Glu Lys Tyr Ile Val His Lys
```

Fig. 8d

```
                                        1302
GAA TTC GAT GAT GAC ACT TAC GAC AAT GAC
Glu Phe Asp Asp Asp Thr Tyr Asp Asn Asp

1332
ATT GCG CTG CTG CAG CTG AAA TCG GAT TCG
Ile Ala Leu Leu Gln Leu Lys Ser Asp Ser

1362
TCC CGC TGT GCC CAG GAG AGC AGC GTG GTC
Ser Arg Cys Ala Gln Glu Ser Ser Val Val

1392
CGC ACT GTG TGC CTT CCC CCG GCG GAC CTG
Arg Thr Val Cys Leu Pro Pro Ala Asp Leu

1422
CAG CTG CCG GAC TGG ACG GAG TGT GAG CTC
Gln Leu Pro Asp Trp Thr Glu Cys Glu Leu

1452
TCC GGC TAC GGC AAG CAT GAG GCC TTG TCT
Ser Gly Tyr Gly Lys His Glu Ala Leu Ser

1482
CCT TTC TAT TCG GAG CGG CTG AAG GAG GCT
Pro Phe Tyr Ser Glu Arg Leu Lys Glu Ala

1512
CAT GTC AGA CTG TAC CCA TCC AGC CGC TGC
His Val Arg Leu Tyr Pro Ser Ser Arg Cys
```

Fig. 8e

```
                                    1542
ACA TCA CAA CAT TTA CTT AAC AGA ACA GTC
Thr Ser Gln His Leu Leu Asn Arg Thr Val

1572
ACC GAC AAC ATG CTG TGT GCT GGA GAC ACT
Thr Asp Asn MET Leu Cys Ala Gly Asp Thr

1602
CGG AGC GGC GGG CCC CAG GCA AAC TTG CAC
Arg Ser Gly Gly Pro Gln Ala Asn Leu His

1632
GAC GCC TGC CAG GGC GAT TCG GGA GGC CCC
Asp Ala Cys Gln Gly Asp Ser Gly Gly Pro

1662
CTG GTG TGT CTG AAC GAT GGC CGC ATG ACT
Leu Val Cys Leu Asn Asp Gly Arg MET Thr

1692
TTG GTG GGC ATC ATC AGC TGG GGC CTG GGC
Leu Val Gly Ile Ile Ser Trp Gly Leu Gly

1722
TGT GGA CAG AAG GAT GTC CCG GGT GTG TAC
Cys Gly Gln Lys Asp Val Pro Gly Val Tyr

1752
ACC AAG GTT ACC AAC TAC CTA GAC TGG ATT
Thr Lys Val Thr Asn Tyr Leu Asp Trp Ile
```

Fig. 8f

```
                                              1783
CGT GAC AAC ATG CGA CCG TGA CCAGGAACAC
Arg Asp Asn MET Arg Pro

1809
CCGACTCCTC AAAAGCAAAT GAGATC

1839
TGGC GGAAGCTTCT GCAGGTCGAC GGATCC
```

Fig. 8g

TRIS-KRINGLE PLASMINOGEN ACTIVATOR WITH NOVEL K2 INSERT

RELATED APPLICATIONS

This application is a continuation-in-part of Ser. No. 06/884,835, filed July 11, 1986 by Paul P. Hung, Narender K. Kalyan and Shawguang L. Lee, now U.S. Pat. No. 4,916,071 granted Apr. 10, 1990;

Copending application Ser. No. 07/8,795, now abandoned by the same inventors discloses certain intermediates used in this application.

Copending application Ser. No. 874,323, filed June 13, 1986, now abandoned discloses the process for site-specific DNA splicing used in this application.

BACKGROUND OF THE INVENTION

Tissue-type plasminogen activator (t-PA), a key enzyme in the thrombolytic system, is endogenously synthesized as a single chain molecule. However, it can be easily converted into two chains by limited proteolytic cleavage with plasmin or trypsin at the amino acid 275-276 site. The light (L) chain, extending toward the C-terminal part of the molecule, contains the catalytic domain. The heavy (H) chain contains three domains identified as the finger (F) domain, the epidermal growth factor (EGF) domain and two kringle (K1 and K2) sequences. Several studies have suggested that fibrin binding specificity, which fixes t-PA to a thrombus in proximity to plasminogen, resides in the F and K domains of the H-chain. Zonneveld et al., Proc. Natl. Acad. Sci. 83 4670 (1986); Vehar et al., Bio/Technology (Dec.) pp. 1051-1062 (1984) and Patthy, Cell, 41 657 (1985).

BRIEF DESCRIPTION OF THE INVENTION

In accordance with this invention, there is provided a group of tissue-type plasminogen activators in which a duplicate second kringle or a modified second kringle has been inserted before the first kringle to create the new kringle domain sequence -K-K1-K2- in which K is K2 or a modification of K2 such that glycosylation at amino acid site 184 is avoided by altering the identity of one of the amino acids at positions 184, 185 or 186. Preferably, the Ser at position 186 is substituted by Ala to avoid glycosylation.

The presence of an additional K2 or its functional equivalent increases fibrin binding affinity, increasing potential fixing of the plasminogen activator at the site of a blood clot for plasmin production and thrombolysis.

This invention also provides the DNA sequences encoding for the novel plasminogen activators, as well as replicable expression vectors containing that DNA.

DESCRIPTION OF THE DRAWINGS

FIG. 3 presents a schematic design description and method of production of the oligonucleotide synthetically prepared to encode for amino acids 192 through 258 found in K2 of t-PA.

FIGS. 8 and 8a-g present the nucleotide sequence of ptPBM-1 which contains DNA coding for the complete t-PA molecule.

METHODS AND MATERIALS

Figure 1:
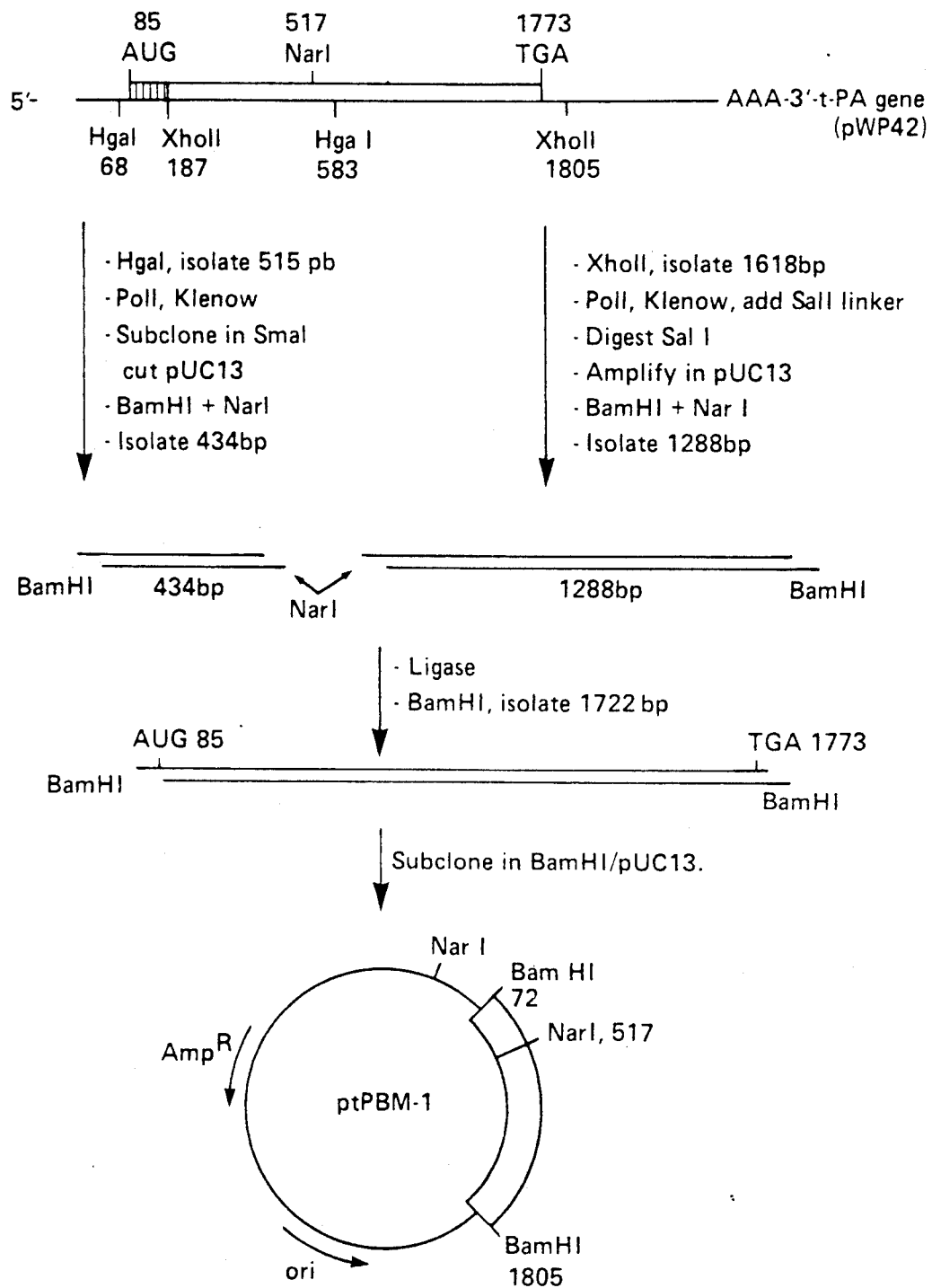
FIG. 1 presents a flow diagram of the method employed in the production of ptPBM-1 which contains DNA encoding the complete t-PA molecule.

The general techniques employed in the manipulation of DNA for use in production of t-PA are as follows:

a) Enzymic Reactions: The restriction and DNA modifying enzymes were obtained from New England Biolabs Inc., Beverly, Mass., or International Biotechnologies Inc., New Haven, Conn. A typical restriction enzyme reaction was performed in a total volume of 50 $\mu$l following the procedure(s) recommended by the supplier of the enzyme.

A ligation reaction for the sticky end DNA is typically performed at 15° C. overnight in a buffered 20 $\mu$l solution containing 100-200 ng DNA and 400 units of T4 DNA ligase (N.E. Biolabs.). For blunt end ligation, 4 units of T4 RNA ligase (N.E. Biolabs.) are included in the above reaction mixture. (Goodman, H.M., and MacDonald, R.J., Method. Enzymol. 68, 75, 1979). The buffer solution used is prepared as a stock 10X solution; 0.5M Tris ®.HCl (pH 7.6), 0.1M MgCl$_2$ and 0.1M DTT (dithiothreitol).

b) Synthesis of Oligonucleotides: All the oligonucleotides mentioned in this application were synthesized by the phosphotriester method (Crea et al., Proc. Nat'l. Acad. Sci. (USA) 75, 5766, 1978) using the Gene Machine model 380A (Applied Biosystems Inc., Foster City, Calif.). Before their use in ligation reactions, the oligomers were phosphorylated at the 5' end in a volume of 50 $\mu$l containing 200-500 ng DNA, 10 units of T4 DNA kinase, 0.5 mM ATP and kinase buffer (0.05M Tris.HCl, pH 7.6, 10 mM MgCl$_2$, 5 mM DTT) and incubated at 37° C. for $\frac{1}{2}$ hour. For use as hybridization probes, oligomers were radiolabeled with 100 $\mu$Ci gamma $^{32}$P-ATP (5,000 Ci/mmol, Amersham, Arlington Heights, Ill.) following the procedure of Maxam, A.M. and Gilbert, W. Methods Enzymol. 65, 499 (1980).

c) Isolation of DNA Fragments: DNA fragments were first separated by electrophoresis through 0.5-1.5% agarose gel. Electrophoresis is carried out at about 100 volts for 2-4 hours in Tris-Borate-EDTA (TBE) buffer (0.089M Tris, 0.089M boric acid, 2 mM EDTA, pH 8.0). DNA bands are visualized under UV light by staining the gel in 0.5 $\mu$g/ml ethidium bromide solution (Sharp et al. Biochem. 12, 3055, 1973). The agarose containing the DNA band is cut out with a razor. The DNA is electroeluted from the gel. (Maniatis et al. Molecular Cloning, a Laboratory Manual, p. 164, 1982). The DNA is further purified by passing it through an Elutip-d ® column (Schleicher and Schuell, Keene, N.H.). The DNA is precipitated with ethanol. After centrifugation in an Eppendorf microfuge for 15 minutes, the pellet is washed once with 70% ethanol, dried under vacuum and dissolved in 50 µl deionized water.

d) Miniplasmid DNA Preparation: About 2 ml of LB (Luria Bertani) medium containing appropriate antibiotics is inoculated with a single bacterial colony and is incubated at 37° C. overnight with vigorous shaking. About 1.5 ml of the culture medium is used to isolate plasmid DNA by the boiling method described in Maniatis et al. loc. cit. p. 366. The rest of the culture is stored in 50% glycerol at −20° C. for later use. The DNA is dissolved in 40 µl H₂O containing 10 µg RNase/ml. About 8 µl is sufficient for one restriction enzyme analysis.

e) Large Scale Preparation of Plasmid DNA: Typically, one liter of LB medium is inoculated with a single bacterial colony. After amplification of the plasmid DNA with chloramphenicol, the bacterial cells are harvested and lysed according to the boiling method (Holmes, D. S. and Quigley, M. Anal. Biochem. 114, 193, 1981). The plasmid DNA is further purified either by cesium chloride gradient centrifugation or by column chromatography on a Sepharose 4B column (Pharmacia, Uppsala, Sweden) as described in Maniatis et al., loc. cit. pp. 93–96. A recovery of about 400 µg DNA per liter culture is routinely obtained.

f) Vectors: dG-tailed pBR322 plasmid DNA (Bethesda Research Laboratories, Inc., Gaithersburg, Md.) was used to clone the cDNA for t-PA. The detailed molecular structure of pBR322 is described by Maniatis et al., loc. cit. pp. 5 and 488. The *E. coli* strains used for transformation with recombinant pBR322 were either HB101 or 294 (Maniatis et al., loc. cit. p. 504).

All subcloning of DNA fragments from the t-PA gene were performed in pUC plasmids—a series of pBR322 derived vectors containing lac Z and ampicillinase genes. These plasmids also contain multiple cloning sites in the lac Z which provides great flexibility in subcloning of DNA sequences (Vieria, J. and Messing, J., Gene 19, 259, 1982). Cloning in any of the available 11 sites can be monitored by the appearance of white recombinant colonies in the background of blue vector colonies on an indicator plate containing X-gal (5-bromo-4-chloro-3-indolyl β-D-galactoside) (Ruther, Mol. Gen. Genetics 178, 475, 1980). The *E. coli* strain used for transformation with the recombinant pUC plasmid, was JM 103.

g) Host/vector System:

1. Microbial System

The work described here was performed using the microorganisms *E. coli* K-12 strain JM 103 (Pharmacia) and *E. coli* K-12 strain 294 (ATCC No. 33625). Other microorganisms which may be used in this process include other useful *E. coli* strains and Bacilli, such as *Bacillus subtilis*. All these microorganisms utilize plasmids that can replicate and express heterologous gene sequences.

The expression system in yeast employs a plasmid which is capable of selection and replication in *E. coli* and/or yeast (*Saccharomyces cerevisiae*). For selection in yeast, the plasmid contains the TRP 1 gene which renders a transformed trp-yeast strain (RH218) prototrophic for tryptophan. The yeast expression vector can shuttle between yeast and *E. coli*. The plasmid has the following components: (1) a DNA segment derived from PBR 322 containing the origin of replication and the ampicillin resistance gene, (2) the yeast TRP 1 gene, (3) the yeast 2 µ DNA which enables the plasmid to replicate in yeast with high stability, (4) a promoter region from the yeast gene, such as alcohol dehydrogenase, α factor, glyceraldehyde-3-phosphate-dehydrogenase, etc., (5) translational start and transcriptional stop sequences which can be used for proper termination and polyadenylation of mRNA in the expression system.

2. Mammalian Cell Culture System

Mammalian cell lines capable of the replication and expression of a compatible vector for the production of heterologous proteins can be used in the present invention. They are, for example: Cos-7, WI38, 3T3, CHO, Hela cells, and C127 cells. The vectors used contain (1) the origin of replication derived from a virus (SV40, adeno, polyoma, BPV) or cellular chromosomal DNA, (2) a promoter, (3) the translational initiation signals, such a ribosomal binding sites, and (4) RNA processing signals, (RNA splicing, polyadenylation and transcriptional terminator sequences). Specific examples of the expression vectors presented here use a BPV viral replication origin, a mouse metallothionein promoter and SV40 RNA processing signals. The vector can also be shuttled between a mammalian cell culture and *E. coli*. It contains derivatives of pBR322 sequences which provide selectable markers for *E. coli* ampicillin resistance as well as an *E. coli* origin of DNA replication. These sequences are derived from the plasmid pML-2d.

The edited hybrid plasminogen activator gene containing a Bam HI sticky end is first inserted at the Bgl II site of plasmid 341-3 (Law MF et al., Md. Cell Biol. F 3, 2110, 1983) between the mouse metallothionein transcriptional promoter element and the SV40 early region transcriptional processing signals. The complete BPV genome, obtained after digestion of plasmid 142-6 (ATCC No. 37134) with Bam HI, is ligated to the unique Bam HI site. Plasmid 341-3 also contains pML2, a pBR322 derivative which allows plasmid replication in bacterial cells. The expression plasmid constructed herein can replicate in mouse C127 cells exclusively as an extrachromosomal episome. Transfected cells can be selected for the transformed phenotype. Further modification of the expression vector, such as by adding specific enhancer elements for higher expression levels or inserting drug resistance (such as neomycin resistance) into the gene is also possible.

DETAILED DESCRIPTION OF THE INVENTION

Several DNA sequences employed in the production of the hybrid t-PA molecule of this invention were obtained from plasmid ptPBM-1 and plasmid ptPFsp-2 which were prepared in the following manner:

t-PA cDNA

Total RNA was isolated by the isothiocyanate method (Maniatis et al., loc. cit. p. 196) from normal human fibroblast cells (WI-38 cells), which had been stimulated by endothelial cell growth factor (ECGF) and heparin to produce t-PA. The same stimulated cells produce urokinase. Messenger RNA (mRNA) was obtained from the total RNA by chromatography on an oligodeoxythymidine (dT)-cellulose column (Aviv et al, Proc. Nat'l. Acad. Sci USA, 69, 1408, 1972). Further fractionation of the mRNA was performed by centrifugation in a 15-30% sucrose density gradient and individual mRNA fractions were hybridized with $^{32}$P-oligo-probes which were complementary to the cDNA sequence of t-PA. Fractions containing the t-PA message (ca. 20-24s) were pooled for use in the preparation of complimentary DNA (cDNA).

Double stranded cDNA, synthesized from 5 μg of pooled mRNA, was inserted into Pst I cut pBR322 using the homopolymeric tailing method (Maniatis et al., loc. cit., p. 229-246). cDNA clones for t-PA and urokinase were identified by in situ hybridization of 10$^5$ clones as described by Pennica, D. et al., Nature, 301, 214, 1983, and Heyneker, H. et al., European Patent Application 92,182 to Genentech Inc., So. San Francisco, Calif. One clone (pWP-42) was found to contain the full length coding sequence for t-PA which was approximately 2,600 bp in length. Another clone pUK53, containing the coding sequence for the urokinase gene, was 1,700 bp in length. After nucleotide sequencing by the Maxam and Gilbert method (Methods Enzymol., 65, 1499, 1980), the 5' end of this gene was found to be missing approximately 30 nucleotides corresponding to the first 10 amino acids of the signal peptide coding region of the urokinase protein.

ptPBM-1

Approximately 10 μg of pWP 42 plasmid DNA was digested with 9 units Xho II at 37° C. for 2 hours. The reaction mixture was run on a preparative 1.2% agarose gel and a 1618 bp DNA fragment was isolated by electroelution. After filling in cohesive ends with *E. coli* Polymerase 1 (Klenow fragment) and dNTPs (four deoxy nucleotide triphosphates—dATP, dGTP, dCTP and dTTP) 1 μg of the so modified DNA was ligated overnight with 300 ng of phosphorylated Sal I linker. After phenol/chloroform extraction and ethanol precipitation, the DNA was digested with 50 U of Sal I for four hours and the reaction mixture applied to a preparative 1% agarose gel to isolate the desired DNA fragment.

The DNA with Sal I ends was ligated to Sal I cut pUC 13 and used to transform *E. coli* JM 103 cells and the cells were plated out on ampicillin and X-gal plates. Eight ampicillin resistant, white colonies were selected and grown to prepare a mini-plasmid preparation. Two clones (ptPS34B and ptPS39) were found to contain the required DNA fragment. Ten μg of ptPS39 plasmid DNA digested to completion with Bam HI and Nar I was run on preparative agarose gel to obtain a 1288 bp fragment coding for the C-terminal end of t-PA.

The 5' end of the t-PA gene was obtained by digestion of 10 μg of pWP 42 with four units of Hga I at 37° C. for eight hours. A 515 bp fragment was isolated by electrophoresis in 1% agarose gel followed by electroelution. The cohesive ends of this DNA fragment were filled in with DNA polymerase 1 (Klenow fragment) and dNTPs and the product was ligated to Sma I cut pUC 13. After transforming *E. coli* JM 103 cells, approximately 75 ampicillin resistant, white colonies were obtained. Twenty four of these colonies were grown to prepare a miniplasmid preparation. The miniplasmid preparation was digested with Nar I and 17 clones were found to have the required insert in either orientation. One clone (ptPHga-4) was grown in 1.0 liter of LB medium containing ampicillin to obtain a large quantity of plasmid DNA using the boiling method. The plasmid DNA, ptPHga 4, was digested with Bam HI and Nar I and electrophoresed on 1.2% agarose gel to isolate a 434 bp DNA fragment coding for the N-terminal end of t-PA.

The 1288 bp DNA (300 ng) and 434 bp DNA (100 ng) were ligated overnight to obtain a 1722 bp DNA fragment. This DNA, after ligation with Bam HI cut pUC 13 was used to transform *E. coli* JM 103 cells. More than 1000 ampicillin resistant colonies were obtained. Plasmid DNA from twelve colonies was prepared. The plasmid DNA was identified by cutting with each of Bam HI, Nar I and Xho II. All of the resulting plasmids were found to contain the desired 1,722 bp DNA fragment. One plasmid (ptPBM-1) was used for large scale plasmid DNA preparation. This plasmid, when cut with Bam HI, gave rise to the 1,722 bp DNA coding for the complete t-PA molecule. The ptPBM-1 clone restriction map and a schematic diagram of its preparation is depicted in FIG. 1.

ptPFsp-2

Figure 2:
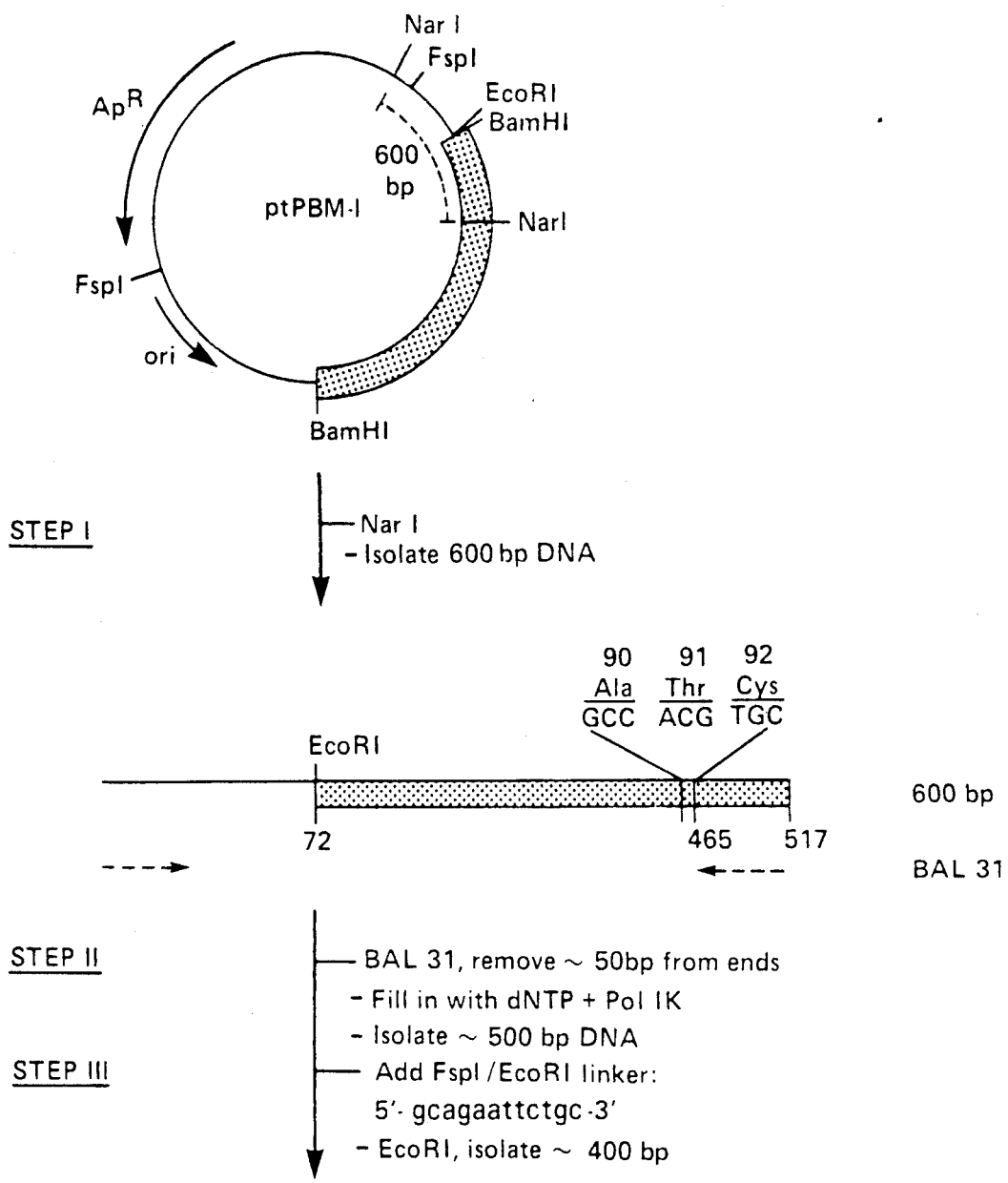
FIGS. 2 and 2A presents a flow diagram of the method employed in the production of the ptPFsp-2 which contains DNA encoding amino acids 1-92 (as well as the complete signal sequence) of t-PA with an Fspl restriction site at bp 465 (a.a. 92).
Figure 2A:
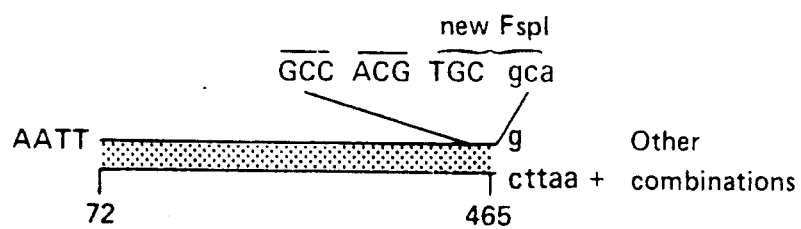
Figure 2A:
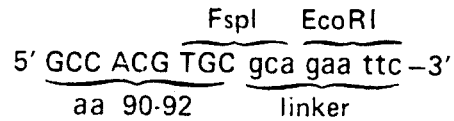
Figure 2A:
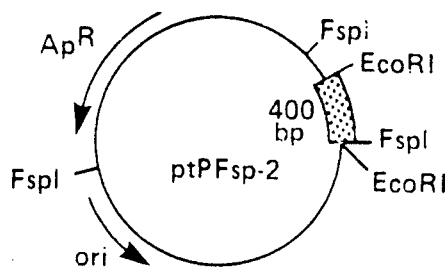

About 10 μg ptPBM-1 plasmid DNA in a 50 μl reaction mixture was digested with Nar I to give rise to two DNA fragments—600 bp and 3,800 bp. The smaller Nar I fragment (600 bp) contained the intended DNA of 400 bp to be isolated. The reaction mixture was diluted to 100 μl volume with BAL 31 buffer to give a final concentration of 10 mM CaCl$_2$, 12 mM MgCl$_2$, 0.2M NaCl, 20 mM Tris-Cl, pH 8.0, 1 mM EDTA. The reaction tube was incubated with 1 μl (2u) of BAL 31 for 10 seconds at 30° C. This incubation time was found to be sufficient for the removal of 50 bp from each end of the 600 bp DNA segment. This resulted in the decrease of the DNA size from 600 bp to 500 bp when run on a 1.2% agarose gel electrophoresis. The reaction was stopped by the addition of 5 μl 0.4M EGTA. After phenol extraction and ethanol precipitation, the DNA was made blunt ended with *E. coli* polymerase 1 (Klenow) and dNTPs (dATP, dCTP, dGTP, dTTP) (Maniatis, et al., loc. cit. p. 109). The DNA was electrophoresed in 1.2% agarose gel and a 500 bp DNA segment was isolated. About 100 ng of this DNA was ligated overnight at 15° C. with 1 μg of FspI/EcoR I oligonucleotide linker. As the name suggests, the linker, gca gaa ttc tgc, was designed to create an Fsp I site (TGC gca) when ligated to DNA ending with the sequence TGC (a.a. 92). In addition, an EcoR I sequence was built into the linker to provide a convenient site for subsequent cloning in an EcoR I/pUC 13 vector. After phenol extraction and ethanol precipitation, the DNA was digested thoroughly with EcoR I and a 400 bp DNA fragment was isolated from 1.2% agarose gel. Equimolar amounts of this DNA and EcoRI cut pUC 13 were ligated and the product was used to transform *E. coli* JM 103. Several thousand recombinant colonies were obtained. About 1,000 colonies in 10 plates were replicated on nitro-cellulose paper and screened by in situ hybridization using a radiolabeled oligonucleotide probe (Grunstein, et al., Proc. Nat'l. Acad. Sci. USA, 72, 3961, 1975). The probe used was 18 nucleotides in length and was designed to represent the nucleotide sequence generated at the DNA/linker junction. This almost ensured the elimination of all unwanted clones with different nucleotide sequences at the DNA/linker junctions. Almost 100 clones gave moderate to strong hybridization signals when exposed to x-ray film. Twelve clones were picked and grown to obtain a miniplasmid preparation. About 8 μl of the plasmid-containing solution was digested with 1 unit of Fsp I. Nine out of 12 clones had the newly generated Fsp I site. Depending upon the orientation of the insert in the vector, Fsp I digestion would show either 550 bp (clone No. 2, 3, 5, 9) or 150 bp (clone No. 1, 7, 8, 11, 12). Final confirmation came from nucleotide sequencing by the Maxam-Gilbert method (Methods Enzymol., 65, 1499, 1980) which showed the presence of an Fsp I recognition sequence TGC GCA in clone 2 which was designated ptPFsp-2 which contains the DNA encoding for amino acids corresponding to the complete signal sequence and amino acids 1-92 of the t-PA gene, with an Fsp I site (TGCGCA) at bp 465 (a.a.92) position (FIG. 2).

pK2*-5

Figure 4:
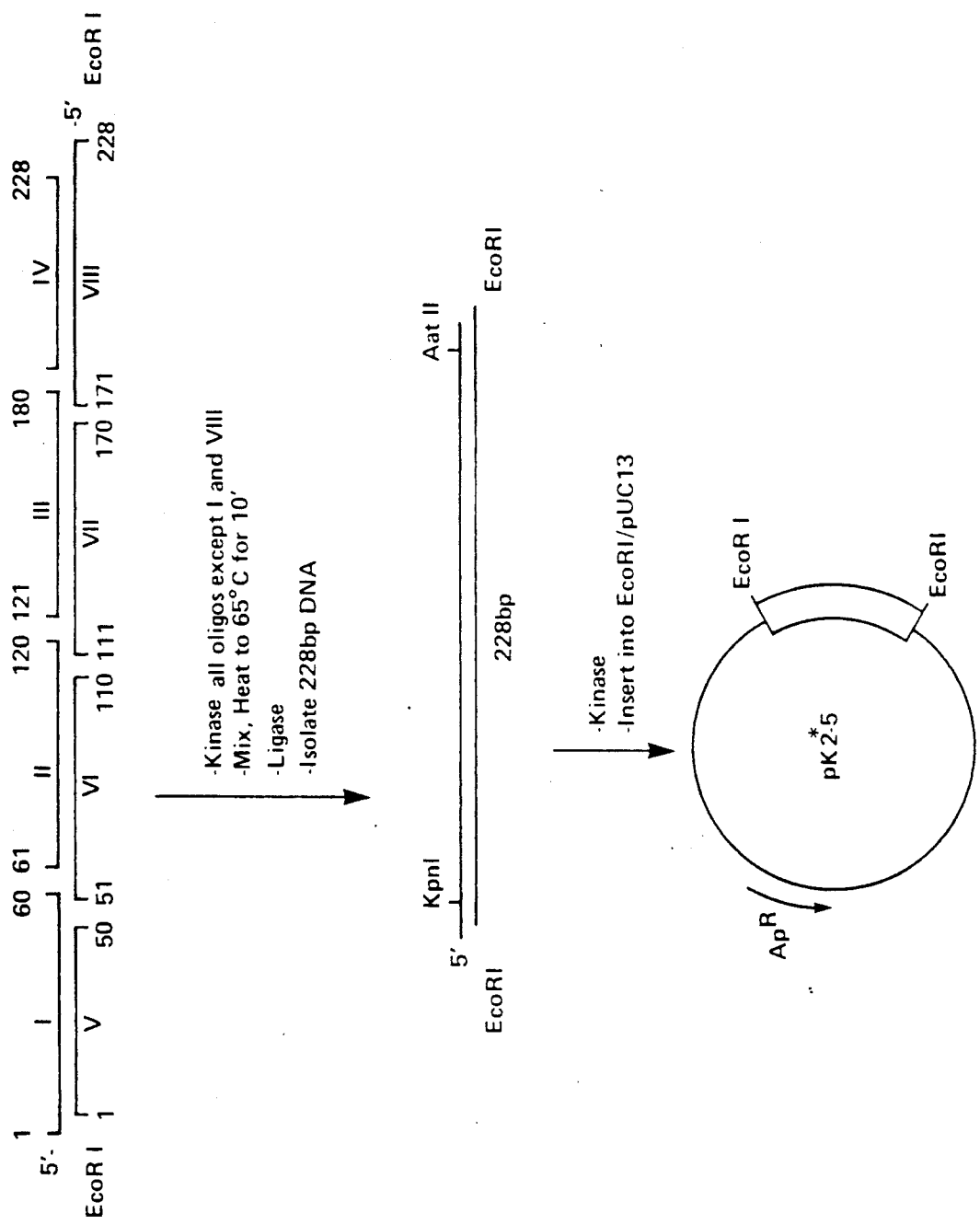
FIG. 4 presents the nucleotide sequence corresponding to fragments I through IV as shown in FIG. 3, which encodes amino acids 192 through 258 found in K2 of t-PA.

The DNA sequence corresponding to amino acids 191 though 258 found in the second kringle (K2) of tissue plasminogen activator (t-PA) as depicted in FIG. 4 was chemically synthesized by the preparation of eight overlapping oligonucleotides on the Gene Machine. The entire nucleotide sequence of oligomers I through VIII is depicted in FIG. 3. Oligomers V through VIII are complementary. A ten nucleotide overlap is provided in each fragment for duplex melding. Oligomers II through VII were phosphorylated with polynucleotide kinase and ATP. The 5'-end of oligos I and VIII were not phosphorylated to avoid self-ligation. All eight oligos were mixed in equal amounts (1 μg of each oligomer), heated to 65° C. for ten minutes for duplex formation among complementary strands and then ligated overnight at 15° C. with T4 DNA ligase. Phenol extraction and ethanol precipitation followed by electrophoresis on agarose gel located a 228 bp DNA product which, by construction was flanked on both 5' and 3' ends with EcoRI restriction sites and contains unique Kpn I and Aat II restriction site toward the 5' and 3' ends, respectively, the latter restriction sites defining the DNA fragment corresponding to a.a. 191 to 258 of t-PA. The 228 bp DNA product was electroeluted, phosphorylated with polynucleotide kinase and inserted into EcoRI cut pUC 13. A miniplasmid preparation from 12 clones was prepared and cut with EcoRI to identify the clones containing the desired 228 bp insert. One clone was chosen and designated pK2*-5. Nucleotide sequencing of the clone showed that the DNA containing the intended sequence was in correct reading frame. This DNA sequence contains alternate codon sequences for the desired amino acids to avoid recombination and looping out during transcription.

The following examples illustrate, without limitation, the process for production of the DNA sequence, polypeptides and replicable expression vectors of this invention.

EXAMPLE 1

91-[Ala$^{186}$-K2]-92-t-PA

About 10 μg of ptPFsp-2 was digested with Fsp-1 to provide a 550 bp DNA fragment encoding for the complete signal peptide (a.a. −35 to −1) and the first 92 amino acids of t-PA with the unique Fsp-1 restriction site at a.a. 92 position. About 1 μg of this DNA was ligated with T4 DNA ligase to 2 μg of duplex oligomer depicted in FIG. 5, produced on the Gene Machine to provide for production of the amino acid sequence -Tyr-Phe-Gly-Asn-Gly-Ala-Ala-Tyr-Arg-Gly-Thr- which corresponds to a.a. 181-191 of the second kringle of t-PA except for the presence of Ala in position 186, and to provide a Kpn-1 site (GGTAC C) at the 3'-terminii. After phenol extraction and ethanol precipitation, the product was cut with Kpn-1 to isolate a 610 bp DNA fraction which was inserted into Kpn-1 cut pK2*-5 to obtain a recombinant clone in which the codon for the N-terminal part of the K2 kringle (a.a. 181-191) was joined to the codon providing amino acid 92 of t-PA. This recombinant clone was designated ptPK2*Kpn-9. It contains the nucleotide sequence encoding the complete signal sequence, a.a. 1-91 followed by a.a. 180-258 of K2 of t-PA. From this plasmid digested with Aat 11 and EcoRI, was obtained the desired 630 bp DNA fragment.

A 330 bp DNA fragment (bp 471-801) containing information coding for a.a. 95 to 205 of t-PA was isolated from EcoRI and Ava 11 cut ptPBM-1. This 330 bp DNA fragment was ligated to a duplex oligomer prepared on the Gene Machine encoding for amino acids 259 to 261 of K2*, the hexapeptide linker encoding for Ser-Glu-Gly-Asn-Ser-Asp and amino acids 92 to 95 of K1 of t-PA. The product was cut with EcoRI and Aat 11 and a 366 bp DNA fragment was isolated, which was ligated to the 630 bp DNA sequence produced in the preceding paragraph to obtain a 996 bp DNA fragment. This DNA sequence was inserted into EcoRI cut pUK 13 for amplification and one recombinant clone was identified which contained the desired product. This clone was labeled p5'HybF-5.

A 1.3 kb fragment of DNA encoding amino acids 110-527 of t-PA was obtained by digesting ptPBM-1 with Bam HI and Nar 1. Digestion of p5'HybF-5 with the same two endonucleases yields a 0.7 kb DNA fragment. Ligation of equal molar amounts of these two DNA fragments followed by digestion of the product with Bam HI provides the complete 2.0 kb genetic material for production of 91-(Ala$^{186}$-K2)-92 t-PA. This genetic material was inserted into Bam HI cut pUC 13 for amplification and one recombinant clone was obtained which contained the complete DNA encoding the desired 91-(Ala$^{186}$-K2)-92 t-PA polypeptide, in correct reading frame. This clone was labeled pHybF-34.

For expression in a mammalia cell expression system, the 2.0 kb gene was inserted in the Bgl II site of the p 341-3 vector, placing it under the control of the metallothionein promotor sequence. At the Bam HI site downstream from the SV-40 poly A adenylation sequence (0.9 kb) was inserted a complete BPV genome (8.0 kb).

This recombinant clone-pHybF-BPV-108 was transfected into mouse C-127 cells followed by conventional culturing, recovery, isolation and purification to afford 91-(Ala$^{186}$K2)-92 t-PA.

EXAMPLE 2

91-(K2)-92-t-PA

Figure 5:
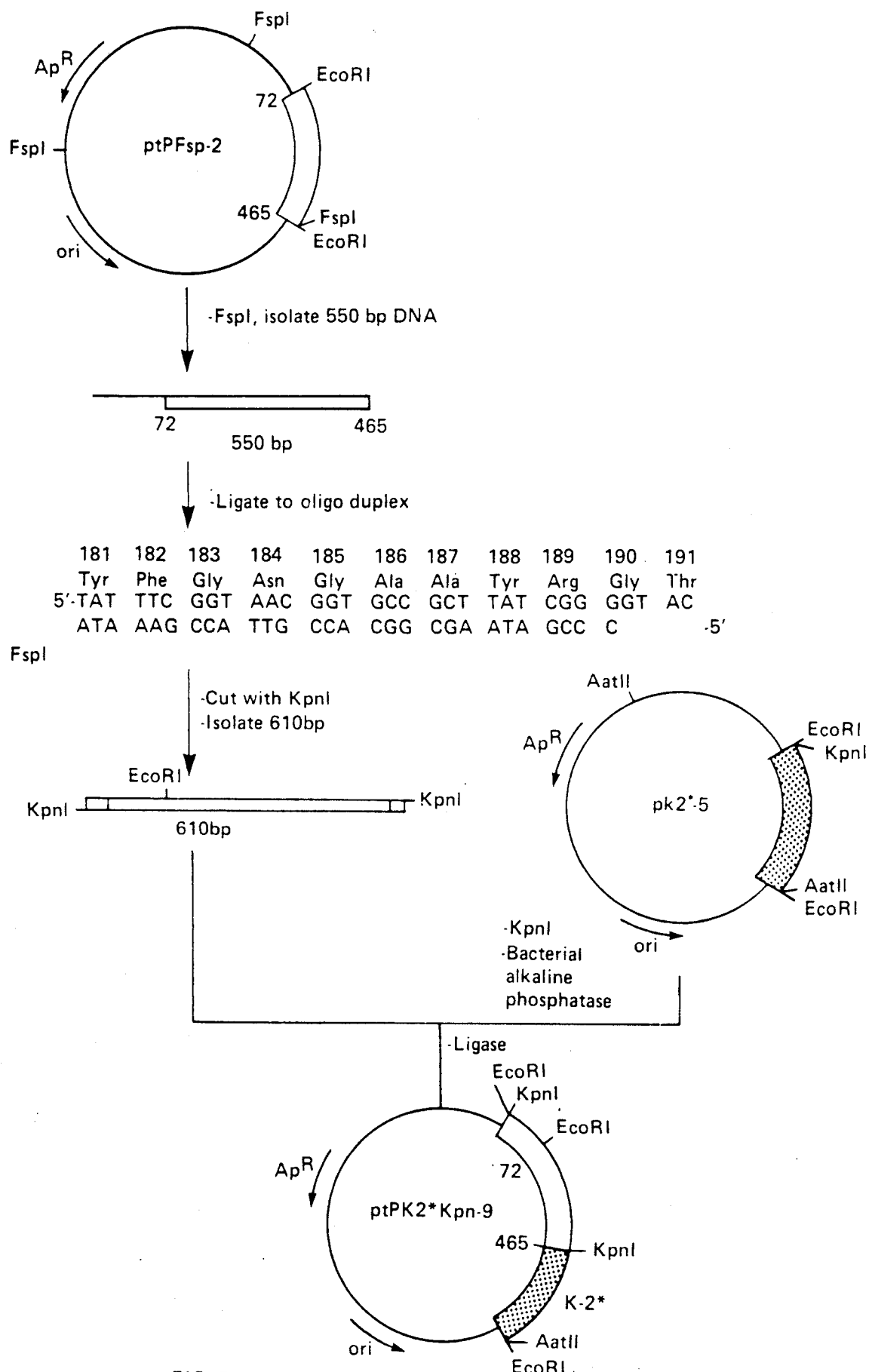
FIGS. 5 and 5a present a flow diagram of the method employed in the production of pHybF-34 which contains the DNA encoding the entire amino acid sequence of 91-(Ala$^{186}$K2)-92-t-PA.
Figure 5A:
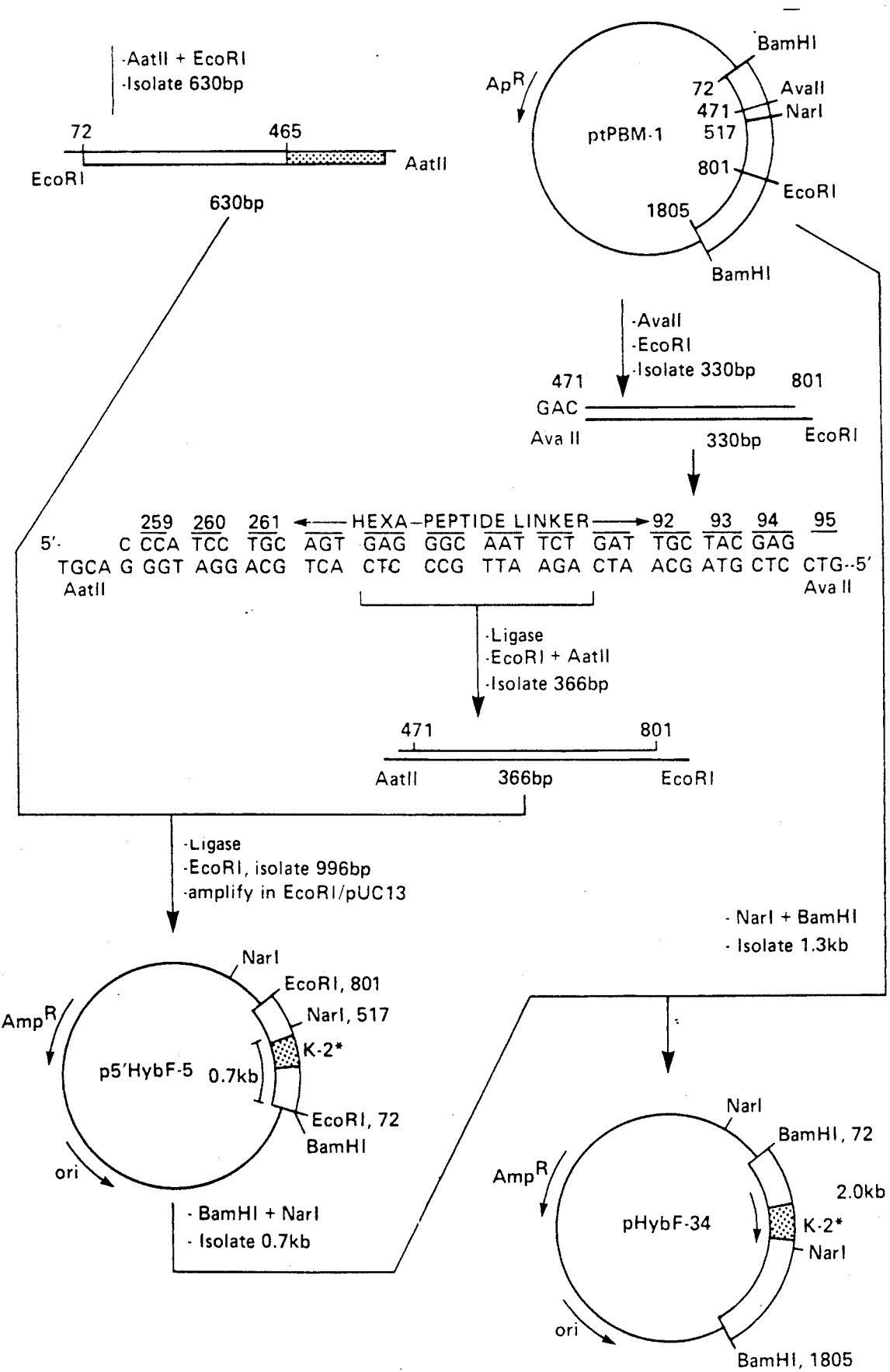

The procedure of Example 1 is followed exactly, as depicted in FIG. 5 and 5a, with the exception that the duplex oligomer shown in FIG. 5 contains the complete DNA sequence encoding a.a. 181-191 of t-PA. Thus, the Ser at position 186 of the polypeptide corresponds to that of the native enzyme, thereby preserving the glycosylation recognition site -Asn-Gly-Ser-. The DNA encoding 91-(K2)-92-t-PA is inserted into the Bam HI cut pUC 13 for amplification. Expression in a mammalian cell system is accomplished following the procedure of Example 1.

The biological properties of the plasminogen activators of this invention were established by determining the relative fibrin clot binding potential and relative plasma clearance rate of the polypeptide produced by the method of Example 1 (Hybrid F), as the representative product, by the following standard experimental test procedures.

Plasma Clearance

Figure 6:
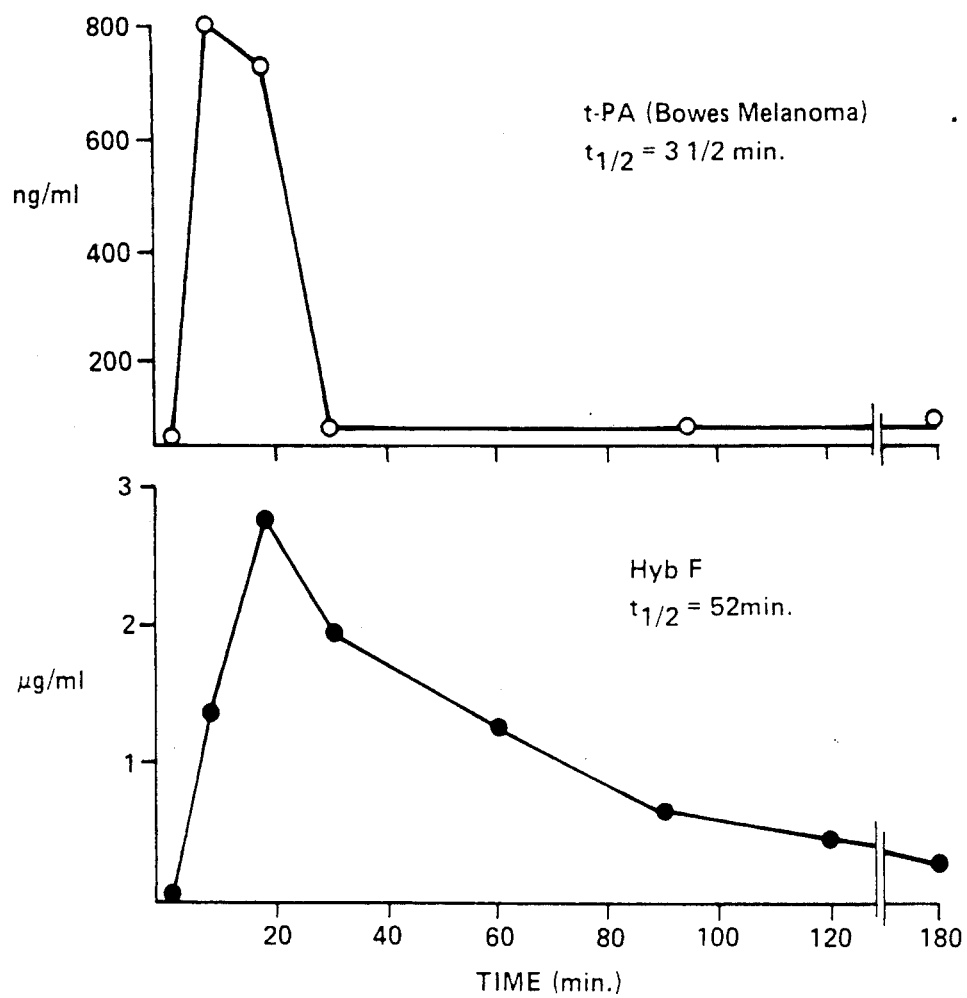
FIG. 6 presents graphs of the plasma concentration of t-PA from Bowes Melanoma and 91-(Ala$^{186}$-K2)-92-t-PA (HybF) of Example 1 versus time for half-life comparison.

Rabbits of about 2.2 kg weight were given 190 μg/kg of Hybrid F or 360 μg/kg of t-PA by infusion over a 15 minute period via an ear vein. Blood samples were collected from the other ear at the time intervals indicated in FIG. 6. Sodium citrate was employed to prevent clotting of the collected blood samples. The drawn blood was immediately centrifuged to separate the plasma and the t-PA related antigens present in the plasma were then determined by t-PA specific ELISA (American Diagnostica, New York, N.Y.). As depicted in FIG. 6, plasma t-PA rapidly increases in concentration to a level of about 0.8 μg/ml and falls very rapidly after the infusion stopped. The half-life for plasma t-PA concentration obtained from these data was about 3.5 minutes which is consistent with the literature. At 30 minutes, the presence of t-PA in the blood was not detectable.

The plasma level of Hybrid F increased in concentration to a level of about 2.8 μg/ml (four times the concentration of t-PA, even at the much lower level of administration) and then slowly disappeared in a biphasic manner over a period of about 120 minutes, to provide a half-life of about 52 minutes. The half-life here is defined as the time required for PA concentration to disappear by 50% after the infusion stopped.

Fibrin Binding

The fibrin binding potential of the representative polypeptide produced in Example 1 (Hyb. F) was compared with Hybrid B and recombinant t-PA to assess relative binding capacity. The procedure employed for evaluating this property of the polypeptides was as follows: A known amount of the plasminogen activator (between 200-400 ng/ml) was mixed with 50 mM Tris®-HCl (pH 7.4), 38 mM NaCl, 100 μ/ml bovine serum albumin and a known amount of plasminogen-free fibrinogen (Miles Laboratories, Elkhart, Ind.) varying from 0 to 1600 μg/ml. The fibrinogen was clotted by addition of thrombin to obtain a final concentration of 1 unit/ml. After incubation for one hour at room temperature, the clot was compacted by centrifugation (6 minutes-microfuge) and unbound plasminogen activator in the supernatant was determined by ELISA.

Alternatively, the bound plasminogen activator was determined in some experiments in which a fixed quantity of 2,000 ng/ml plasminogen activator is employed, by washing the clot pellet with 50 mM Tris-HCl (pH 7.4) buffer containing 38 mM NaCl and the bound plasminogen activator was eluted from the clot with 0.5M L-arginine in the same buffer.

Figure 7:
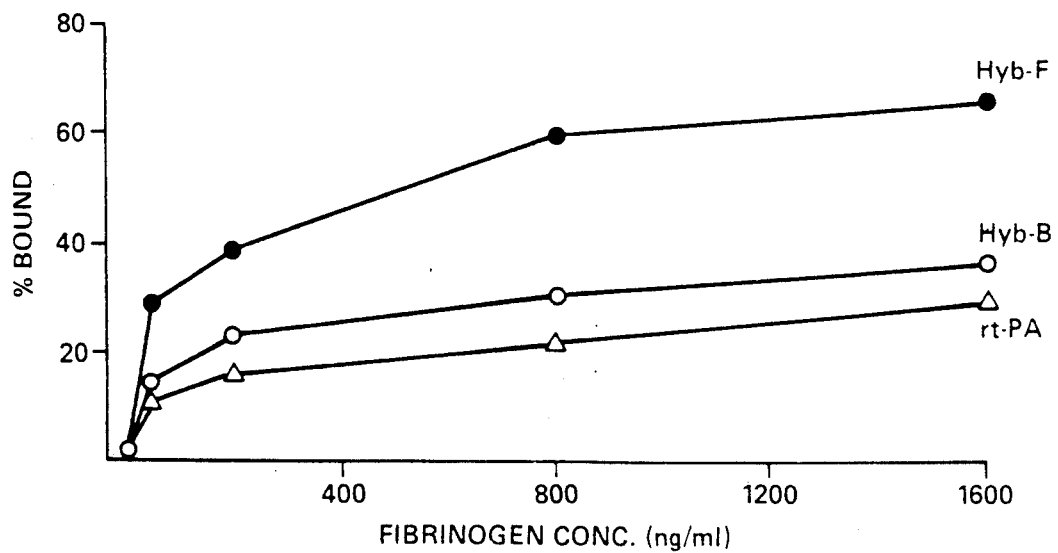
FIG. 7 is a graph comparing the fibrin binding potential of recombinant t-PA (rt-PA), 91-(UKaa$^{50-131}$-Ser-Glu-Gly-Asn-Ser-Asp)-92-t-PA (Hyb B) and 91-(Ala$^{186}$-K2)-92-t-PA (HybF) of Example 1.

In either case (clot bound or unbound), equal volumes of plasminogen activator containing solution were analyzed by SDS-Page followed by fibrin autography. The results of these experiments is graphically depicted in FIG. 7 where it can be seen that between about 30-35 percent of the recombinant t-PA and Hybrid B bound to the fibrin clot whereas Hybrid F of this invention consistently bound better to the fibrin clot. At 1600 ng./ml., the highest fibrinogen concentration studied, more than 60 percent of the Hybrid F molecule present was bound to fibrin.

The tris-kringle plasminogen activators of this invention are useful in the treatment of vascular accidents in mammals in the same manner and through the same delivery vehicles as t-PA itself. The tris-kringle plasminogen activators of this invention may be formulated into pharmaceutical compositions by dissolving or suspending the polypeptides in suitable pharmaceutically acceptable vehicles known to the art as applied to t-PA. For example, the hybrid tissue plasminogen activator of this invention may be lyophilized with physiologic phosphate buffer saline (PBS) containing 0.01% Tween® 80, and dissolved in sterile water to afford an isotonic solution containing from about 5 to about 10 mg/ml of active ingredient. Administration to a mammal in need thereof by intravascular injection or infusion is conducted following techniques already established with t-PA, although a smaller total quantity of the compounds of this invention are needed to achieve the results obtained with t-PA. Hence, an intravenous primary dose of about from 110 to 440 IU/kg body weight followed by continuous infusion of about 110 to 440 IU/kg/hr for about 6 to 12 hours depending upon the response rate of the individual patient is currently consistent with regimens involved in disruption of a thrombosis, the higher doses indicated being that employed with t-PA itself.

The gene coding for the polypeptide produced in Example 1, inserted in the BPV dependent expression system (pHybF-BPV-108) and transfected into E. coli HB-101 was deposited with the American Type Culture Collection, 12301 Parklawn Drive, Rockville, Md. 20852, on Dec. 4, 1987 and assigned accession number ATCC 67570.

What is claimed is:

1. A tris-kringle tissue plasminogen activator comprising the amino acid sequence of human t-PA modified in by insertion of K between amino acids 91 and 92 of human t-PA which K is K2 or K2 modified at position 186 by Ala substitution for Ser to prevent glycosylation, where K2 is the second kringle of human t-PA.

2. The tris-kringle tissue plasminogen activator of claim 1 which is human t-PA with an additional K2 kringle between amino acids 91 and 92 of the formula:

91-(K2)-92-t-PA.

3. The tris-kringle tissue plasminogen activator of claim 1, which is human t-PA with an additional kringle inserted between amino acids 91 and 92, which additional kringle is Ala$^{186}$K2, of the formula:

91-(Ala$^{186}$K2)-92-t-PA.

4. A DNA sequence having a nucleotide sequence that encodes for a plasminogen activator of any one of claims 1-3.

5. A replicable expression vector containing a DNA sequence having a nucleotide sequence that encodes for a plasminogen activator of any one of claims 1-3

6. A pharmaceutical composition comprising a blood clot disrupting amount of a tris-kringle tissue plasminogen activator comprising the amino acid sequence of human t-PA modified by insertion of K between amino acids 91 and 92 of human t-PA in which K is K2 or K2 modified at position 186 by Ala substitution for Ser to prevent glycosylation, where K2 is the second kringle of human t-PA and a pharmaceutically acceptable carrier.

* * * * *